United States Patent
Ogawa et al.

[11] Patent Number: 6,130,329
[45] Date of Patent: *Oct. 10, 2000

[54] PROCESS FOR REDUCING THE VISCOSITY OF AN AQUEOUS SOLUTION OF A FATTY ESTER OF SUCROSE AND USE THEREOF AS AN EMULSIFYING AGENT

[75] Inventors: Akihiro Ogawa; Naoya Otomo; Toru Tagawa, all of Kanagawa, Japan

[73] Assignee: Mitsubishi Chemical Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/941,538

[22] Filed: Sep. 30, 1997

[30] Foreign Application Priority Data

Oct. 7, 1996 [JP] Japan .................................. 8-282890

[51] Int. Cl.[7] .............................. C07H 1/00; C07H 13/02; C07H 13/06
[52] U.S. Cl. .......................................... 536/124; 536/119
[58] Field of Search .................................... 536/124, 119

[56] References Cited

U.S. PATENT DOCUMENTS

| | | | |
|---|---|---|---|
| 5,274,079 | 12/1993 | Katayama et al. ...................... | 530/372 |
| 5,334,679 | 8/1994 | Yamamoto et al. ...................... | 526/200 |
| 5,362,762 | 11/1994 | Beshouri ................................... | 521/64 |
| 5,366,661 | 11/1994 | Katayama et al. ...................... | 252/314 |

FOREIGN PATENT DOCUMENTS 6801834  8/1968  South Africa .

*Primary Examiner*—Howard C. Lee
*Assistant Examiner*—Everett White
*Attorney, Agent, or Firm*—Sughrue, Mion, Zinn, Macpeak & Seas, PLLC

[57] ABSTRACT

An anionic surface active agent such as the monoglyceride of succinic acid is incorporated into an aqueous solution of a fatty ester of sucrose to prepare an aqueous solution of a fatty ester of sucrose having a reduced viscosity. A process for reducing the viscosity of an aqueous solution of a fatty ester of sucrose is disclosed, which comprises incorporating an anionic surface active agent in an aqueous solution containing from 8 to 50% by weight of a fatty ester of sucrose having an HLB of from 5 to 20 in an amount of from 1 to 50 parts by weight based on 100 parts by weight of the fatty ester of sucrose. A novel process is also provided, which comprises the use of an aqueous solution of a fatty ester of sucrose having a viscosity thus reduced as an emulsifying agent for dispersing a sparingly water-soluble particulate inorganic compound or cosmetic material therein.

13 Claims, 1 Drawing Sheet

PROCESS FOR REDUCING THE VISCOSITY OF AN AQUEOUS SOLUTION OF A FATTY ESTER OF SUCROSE AND USE THEREOF AS AN EMULSIFYING AGENT

FIELD OF THE INVENTION

The present invention relates to a process for reducing the viscosity of an aqueous solution of a fatty ester of sucrose (a sucrose ester of fatty acid) and a process which concerns the use of an aqueous solution of a fatty ester of sucrose having a viscosity thus reduced as an emulsifying agent for dispersing various substances which are sparingly soluble in water including particulate inorganic compounds, cosmetic materials, pharmaceuticals, food, etc. More particularly, the present invention relates to a process which comprises reducing the viscosity of a highly concentrated aqueous solution of a fatty ester of sucrose for use in emulsification, dispersion and solubilization. The highly concentrated aqueous solution of a fatty ester of sucrose has improved storability and improved workability during stirring and mixing.

BACKGROUND OF THE INVENTION

A fatty ester of sucrose finds wide application in the fields of food, cosmetics, pharmaceuticals, chemical industry, etc. for many purposes such as emulsification, solubilization, dispersion, antibacterial treatment and inhibition of crystal growth. By properly selecting the substitution degree and kind of fatty acid constituting the fatty ester of sucrose, a fatty ester of sucrose having a wide range of HLB (hydrophilic-lipophilic balance) values can be prepared. Furthermore, a fatty ester of sucrose having a low HLB value can be dissolved in an organic solvent while one having a high HLB value can be dissolved in water or an alcohol. Therefore, these fatty esters of sucrose can be appropriately selected depending on the intended application. In the food industry, for example, a fatty ester of sucrose having a high HLB value is used in an amount of from 400 to 1,000 ppm for antibacterial effect in drinks such as coffee and black tea with dairy ingredient. A fatty ester of sucrose having a low HLB value is used in an amount of from 0.2 to 2% by weight for inhibiting the crystal growth of fats and oils in chocolate, etc.

In general, however, if a fatty ester of sucrose is used in the form of an aqueous solution, the greater the HLB or concentration of the fatty ester of sucrose as a solute, the higher the viscosity of the resulting aqueous solution. Therefore, the preparation of such an aqueous solution of a fatty ester of sucrose requires a large amount of energy and considerable time. Furthermore, it can be difficult to handle such an aqueous solution of a fatty ester of sucrose in various operations. For example, it is difficult to transfer a viscous solution of a fatty ester of sucrose. Accordingly, when used for the foregoing purposes, a dilute aqueous solution of a fatty ester of sucrose having a low viscosity is generally selected.

On the other hand, if whipped cream is prepared from raw cream, 45% of an oil component and 55% of an aqueous component (serum including sugar, protein, etc.) are used as raw materials to produce a product having an oil content of about 40%. In other words, the maximum amount of additional water which can be used is 12.5 parts by weight based on 100 parts by weight of the raw materials. Therefore, if a fatty ester of sucrose is to be added in an amount of about 1% based on the total weight of the system, it is necessary to prepare an aqueous solution of a fatty ester of sucrose having a concentration of about 8%.

Furthermore, a fatty ester of sucrose contains a hydroxyl group as a hydrophilic group and thus does not have the disadvantages of a poly(oxyethylene)derivatives emulsifying agent that loses emulsifying ability at high temperature due to the presence of cloud point. Therefore, the fatty ester of sucrose is advantageous in that the resulting emulsion has high heat stability. A fatty ester of sucrose, also, exhibits high biodegradability and a low stimulating action on the skin, thus it suits for cosmetics and medicines for external application.

In the field of cosmetic materials and pharmaceuticals, if an oil-in-water type emulsion having a high oil phase content such as a skin cosmetic [cream: JP-B-59-14019 (The term "JP-B" as used herein means an "examined Japanese patent publication"), Takeo Mitsui, "New Cosmetic Chemistry", page 349, May 10, 1994, Nanzando] or a liquid hair cream (JP-B-60-31802) is produced, the water content is limited. Therefore, it is necessary to use a highly concentrated aqueous solution of an emulsifying agent as a dispersing emulsifying agent. Accordingly, an aqueous solution of an emulsifying agent containing a fatty ester of sucrose having a concentration of not less than 8% by weight has been desired.

Also if a fatty ester of sucrose is stored in the form of a highly concentrated aqueous solution, problems arise due to high viscosity. Thus, hitherto, a fatty ester of sucrose had to be stored as a dilute aqueous solution having a concentration, for example, of not more than about 5%.

SUMMARY OF THE INVENTION

It is therefore an object of the present invention to provide a process for reducing the viscosity of an aqueous solution of a fatty ester of sucrose which can inhibit the high viscosity of the aqueous solution even if the concentration of the fatty ester of sucrose in the aqueous solution is 8% or more by weight.

The foregoing object of the present invention will become more apparent from the following detailed description and Examples.

The inventors extensively studied viscosity depressants for aqueous solutions of a fatty ester of sucrose to solve the foregoing problems of the prior art. As a result, the present inventors discovered that the viscosity of a concentrated aqueous solution of a fatty ester of sucrose can be reduced to thereby improve its preservability and workability by adding thereto an anionic surface active agent as a viscosity depressant. Thus, the present invention has been achieved based on the above finding.

The present invention provides a process for reducing the viscosity of an aqueous solution of a fatty ester of sucrose, which comprises incorporating an anionic surface active agent into an aqueous solution containing from 8 to 50% by weight of a fatty ester of sucrose having an HLB of from 5 to 20 in an amount of from 1 to 50 parts by weight based on 100 parts by weight of said fatty ester of sucrose.

The present invention also provides a process for dispersing a particulate inorganic compound, cosmetic material or substance which is sparingly soluble in water which comprises (a) providing as an emulsifying agent consisting essentially of an aqueous solution containing from 8 to 50% by weight of a fatty ester of sucrose having an HLB of from 5 to 20 and an anionic surface active agent in an amount of from 1 to 50 parts by weight based on 100 parts by weight of said fatty ester of sucrose; and (b) dispersing said inorganic compound, cosmetic material or substance which is sparingly soluble in water in a media containing said emulsifying agent.

BRIEF DESCRIPTION OF THE DRAWING

By way of example and to make the description more clear, reference is made to the accompanying drawing in which.

DETAILED DESCRIPTION OF THE INVENTION

Figure 1:
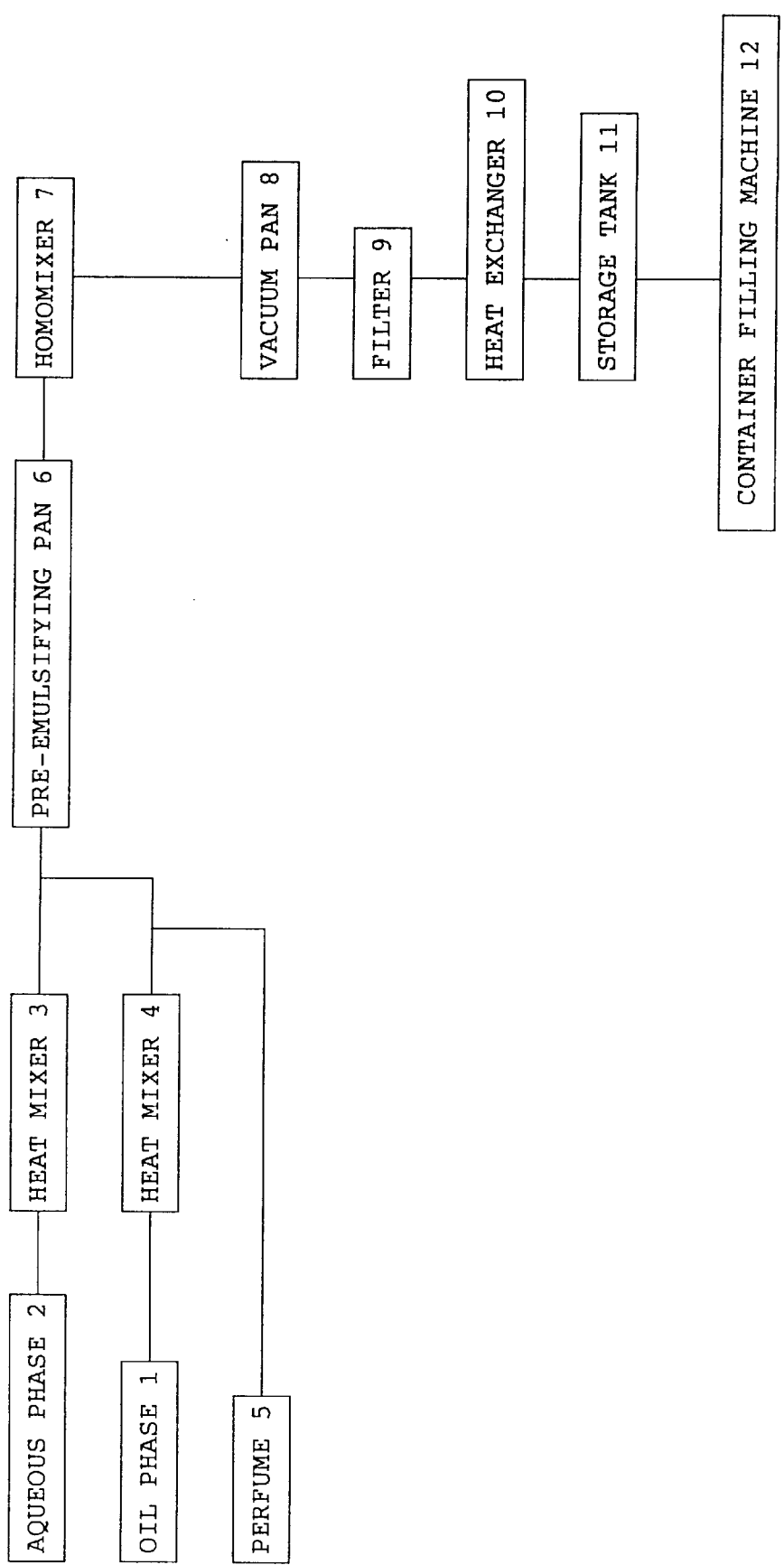
FIG. 1 is a flow chart illustrating the production process for a cosmetic cream.

The present invention is described in greater detail below.

FIG. 1 is a flow chart of the process for the preparation of a cream. In FIG. 1, the reference numeral 1 indicates an oil phase component. The reference numeral 2 indicates an aqueous phase component. The reference numerals 3 and 4 each indicates a mixer equipped with a heater. The reference numeral 5 indicates a perfume. The reference numeral 6 indicates a pre-emulsifying pan. The reference numeral 7 indicates a homomixer. The reference numeral 8 indicates a vacuum pan. The reference numeral 9 indicates a filter. The reference numeral 10 indicates a heat exchanger. The reference numeral 11 indicates a storage tank. The reference numeral 12 indicates a container filling machine.

In order to prepare an oil-in-water type cream, a water-retaining agent such as propylene glycol, an aqueous solution of an emulsifying agent and other water-soluble components are added to distilled water which is then heated to a temperature of about 70° C. to prepare an aqueous phase 2.

Separately, a solid oil component, a semisolid oil component, a liquid oil component, an antiseptic, an oxidation inhibitor, etc. are heated to a temperature of from 70° C. to 80° C. with stirring to make a solution. A perfume 5 is then added to the solution shortly before emulsification. The mixture is then stirred to prepare an oil phase 1.

To the aqueous phase 2 which has previously been prepared, the oil phase 1 is then gradually added dropwise with stirring to effect pre-emulsification at the pre-emulsifying pan 6. Thereafter, the mixture is subjected to emulsification in the homomixer 7 to homogenize the emulsified particles. The emulsion is then subjected to dearation in the vacuum pan 8, filtration through the filter 9 and cooling in the heat exchanger 10. The emulsion is then transferred to the storage tank 11 from which the resulting cream is then poured into a container.

Examples of the anionic surface active agent for use in the present invention as an effective component of the viscosity depressant for the aqueous solution of a fatty ester of sucrose include fatty acid salts; salts of dicarboxylic acid half-ester of long-chain aliphatic alcohol such as stearyl ester of fumaric acid; salts of fatty ester of hydroxycarboxylic acid such as lactylate fatty acid, stearoyl tartaric acid and stearoyl citric acid; salts of polycarboxylic acid ester of monoglyceride such as the monoglyceride of citric acid, the monoglyceride of succinic acid and the monoglyceride of diacetyltartaric acid; salts of long-chain alkylester of sulfosuccinic acid such as dioctylsulfosuccinate; salts of alkylsulfates such as sodium laurylsulfate; salts of monoglyceridephosphates such as sodium monoglyceridephosphate and ammonium monoglyceridephosphate; and lecithin compounds such as lecithin (e.g., vegetable, egg yolk, fractional lecithin) and lysolecithin.

The fatty acid constituting the anionic surface active agent is not particularly limited. In practice, however, a $C_{8-22}$ straight-chain or branched fatty acid may be used. Examples of such a fatty acid include caprylic acid, capric acid, lauric acid, myristic acid, stearic acid, arachidic acid, oleic acid, elaidic acid, ricinoleic acid and 2-butyloctanoic acid. The hydroxycarboxylic acid constituting the anionic surface active agent is a $C_{3-10}$ fatty carboxylic acid containing from 1 to 3 hydroxyl groups and from 1 to 3 carboxylic acid groups per molecule. The base constituting the anionic surface active agent may be an alkali metal such as sodium and potassium, triethanolamine or the like. Preferred among these bases is potassium from the standpoint of its viscosity reducing effect. These anionic surface active agents may be used singly. Alternatively, two or more of these anionic surface active agents may be used in combination and in an arbitrary ratio.

If the monoglyceride of citric acid, the monoglyceride of succinic acid, the monoglyceride of diacetyltartartic acid or the like is sparingly soluble in water, an alkali such as potassium carbonate may be added to the composition to dissociate protons of the carboxylic acid, to thereby improve the solubility of the anionic surface active agent. Particularly preferred among these anionic surface active agents are the monoglyceride of succinic acid and the lactylate fatty acid because they can remarkably reduce the viscosity of a highly concentrated aqueous solution of a fatty ester of sucrose.

Cationic surface active agents such as alkyltrimethyl ammonium chloride and dialkyldimethylammonium chloride and nonionic surface active agents such as poly (oxyethylene)-lauryl ether, the monoglyceride of stearic acid and the diglyceride of stearic acid exert no viscosity reducing effect in an aqueous solution of a fatty ester of sucrose.

The fatty ester of sucrose for use in the present invention may be a water-soluble fatty ester of sucrose having an HLB of from 5 to 20.

The fatty acid constituting the fatty ester of sucrose is not particularly limited. The fatty acid may be selected from the group consisting of $C_{10-30}$, preferably $C_{12-22}$ saturated or unsaturated fatty acids such as lauric acid, myristic acid, palmitic acid, oleic acid, stearic acid and erucic acid. These fatty acids may be used singly. Alternatively, two or more of these fatty acids may be used in any proportion depending on the intended application. In particular, the effect of the present invention of reducing viscosity is remarkable when a fatty ester of sucrose containing a long-chain fatty acid and having 16 or more carbon atoms, particularly a fatty ester of sucrose constituted by a carboxylic acid consisting of from 50 to 90% by weight of stearic acid and from 10 to 50% by weight of palmitic acid is used.

The anionic surface active agent is used in an amount of from 1 to 50 parts by weight, preferably from 5 to 20 parts by weight based on 100 parts by weight of the fatty ester of sucrose in the aqueous solution of a fatty ester of sucrose. If the content of the anionic surface active agent falls below the above defined range (1 part by weight), the resulting aqueous solution of a fatty ester of sucrose cannot exert a viscosity reducing effect. If the content of the anionic surface active agent exceeds the above defined range (50 parts by weight), a viscosity reducing effect is not so significant. Furthermore, the properties of the fatty ester of sucrose itself may be adversely affected.

Examples of the process for reducing the viscosity of an aqueous solution of a fatty ester of sucrose include a process which comprises preparing a highly concentrated aqueous solution of a fatty ester of sucrose, and then mixing the aqueous solution with the anionic surface active agent, and a process which comprises adding water to a mixture of a fatty ester of sucrose and an anionic surface active agent to prepare an aqueous solution. The latter process can be easily effected from the standpoint of ease of operation.

In the foregoing procedure, the aqueous solution obtained by mixing a fatty ester of sucrose with an anionic surface active agent is preferably heated to a temperature of from 70° C. to 80° C. so that the fatty ester of sucrose is dissolved in water, and then rapidly cooled to a temperature of from 15° C. to 20° C. If the aqueous solution is cooled at a low rate, the aqueous solution shows little or no decrease in viscosity drop and thus gels in some cases.

In accordance with the process for reducing the viscosity of an aqueous solution of a fatty ester of sucrose of the present invention, the resulting aqueous solution of a fatty ester of sucrose can exhibit a remarkably reduced viscosity of not more than ⅔ that of an aqueous solution of a fatty ester of sucrose having the same concentration but free of an anionic surface active agent. The effect of the anionic surface active agent in reducing viscosity is surprisingly peculiar to an aqueous solution of a fatty ester of sucrose. The anionic surface active agent does not reduce but rather increases the viscosity of an aqueous solution of a sugar ester other than sucrose made of the same kind of fatty acid as the fatty ester of sucrose, such as the fatty ester of sorbitan.

Furthermore, the anionic surface active agent does not deteriorate the properties of the aqueous solution of a fatty ester of sucrose as the emulsifying agent for dispersion, antibacterial agent or the like. Therefore, the aqueous solution of a fatty ester of sucrose containing the anionic surface active agent is extremely useful as an emulsifying agent or antibacterial agent in the field of particulate inorganic compounds, cosmetic materials, pharmaceuticals, milk drinks containing calcium carbonate or calcium phosphate, etc.

An example of the formulation of the aqueous solution of a fatty ester of sucrose having a reduced viscosity by incorporating therein an anionic surface active agent used in an amount of from 1 to 20 parts by weight based on 100 parts by weight of the fatty ester of sucrose in the aqueous solution is given below.

| Fatty ester of sucrose | 8–45.5 wt % |
|---|---|
| Anionic surface active agent | 0.1–9 wt % |
| Water | 45.5–91.9 wt % |

The concentration of the fatty ester of sucrose in the foregoing aqueous solution depends on the kind of the fatty ester of sucrose and cannot be unequivocally determined. In practice, however, the concentration of the fatty ester of sucrose in the aqueous solution of a fatty ester of sucrose is generally from 8 to 45.5% by weight, preferably from 10 to 40% by weight. The lowest concentration of the aqueous solution of a fatty ester of sucrose at which the workability of the composition is adversely affected because of increased viscosity is normally about 8% by weight, although this depends somewhat on its HLB. Accordingly, the viscosity of an aqueous solution of a fatty ester of sucrose having a concentration of from about 8 to 45.5% by weight can be remarkably reduced by adding the foregoing viscosity depressant. An aqueous solution of a fatty ester of sucrose having a concentration of 50% or more by weight, particularly containing a fatty ester of sucrose having a long-chain fatty acid, is in a slurry form or in a form close to a solid rather than an aqueous solution. The viscosity of such an aqueous solution often cannot be reduced by the addition of the foregoing viscosity depressant no matter how much is added.

The viscosity of the aqueous solution of a fatty ester of sucrose is not more than 10,000 centipoise (cps), preferably from 2 to 150 cps if it is used as an emulsifying agent for an inorganic salt such as calcium carbonate, determined at a temperature of 15° C. by an E type rotary viscometer.

The aqueous solution of a fatty ester of sucrose can be used for dispersing inorganic particulate material such as particulate calcium carbonate and barium sulfate, or as an emulsifying agent or an antibacterial agent for cosmetic materials or pharmaceuticals.

The present invention will be further described in the following Examples, but the present invention should not be construed as being limited thereto. The term "ratio" and "parts" as used herein are by weight.

Method of Viscosity Evaluation:

A highly concentrated aqueous solution of a fatty ester of sucrose is freshly prepared. The viscosity of the solution is measured at a temperature of 15° C. by means of an E type rotary viscometer (VISCONIC (trade name), ELD type, EMD type and EHD type, manufactured by Tokyo Keiki Co., Ltd., unit: centipoise (cp)). For comparison, the viscosity of a highly concentrated aqueous solution of a fatty ester of sucrose free of an anionic surface active agent (viscosity depressant) is measured in the same manner as above.

EXAMPLE 1

To 9.5 parts of Ryoto Sugar Ester S-1670 (a fatty ester of sucrose available from Mitsubishi-Kagaku Foods Corporation; HLB: 16, stearic acid content: 70%, palmitic acid content: 30%) were added 90 parts of water. The mixture was then stirred. To the mixture was then added 0.5 part (5.3% based on the weight of the fatty ester of sucrose) of the monoglyceride of succinic acid (SMG) as a viscosity depressant.

The mixture was heated to a temperature of from 70° C. to 80° C. and stirred at this temperature for 20 minutes to make a solution. The solution was then rapidly cooled to a temperature of 15° C. to obtain an aqueous solution of a fatty ester of sucrose having a concentration of 9.5%. The viscosity of the aqueous solution of a fatty ester of sucrose thus prepared comprising a viscosity depressant incorporated therein was then measured. The results are set forth in Table 1.

COMPARATIVE EXAMPLE 1

The procedure of Example 1 was followed except that the viscosity depressant (monoglyceride of succinic acid) was not added and using 90.5 parts of water. The viscosity of the aqueous solution of a fatty ester of sucrose thus prepared was then measured. The results are set forth in Table 1.

COMPARATIVE EXAMPLE 2

The procedure of Example 1 was followed except that poly(oxyethylene)lauryl ether was used as a nonionic surface active agent instead of the monoglyceride of succinic acid. The viscosity of the aqueous solution of a fatty ester of sucrose thus prepared was then measured. The results are set forth in Table 1.

EXAMPLE 2

The procedure of Example 1 was followed except that Ryoto Sugar Ester S-1170 (a fatty ester of sucrose available from Mitsubishi-Kagaku Foods Corporation; HLB: 11, stearic acid content: 70%, palmitic acid content: 30%) was used as the fatty ester of sucrose. The viscosity of the aqueous solution of a fatty ester of sucrose having a concentration of 9.5% thus prepared was then measured. The results are set forth in Table 1.

COMPARATIVE EXAMPLE 3

The procedure of Example 2 was followed except that the viscosity depressant (monoglyceride of succinic acid) was not added. The viscosity of the aqueous solution of a fatty ester of sucrose thus prepared was then measured. The results are set forth in Table 1.

EXAMPLE 3

The procedure of Example 1 was followed except that Ryoto Sugar Ester P-599 (a fatty ester of sucrose available from Mitsubishi-Kagaku Foods Corporation; HLB: 5, palmitic acid content: not less than 99%) was used as the fatty ester of sucrose. The viscosity of the aqueous solution of a fatty ester of sucrose having a concentration of 9.5% thus prepared was then measured. The results are set forth in Table 1.

COMPARATIVE EXAMPLE 4

The procedure of Example 3 was followed except that the viscosity depressant (monoglyceride of succinic acid) was not added. The viscosity of the aqueous solution of a fatty ester of sucrose thus prepared was then measured. The results are set forth in Table 1.

EXAMPLE 4

The procedure of Example 1 was followed except that Ryoto Sugar Ester M-590 (a fatty ester of sucrose available from Mitsubishi-Kagaku Foods Corporation; HLB: 5, myristic acid content: 90%) was used as the fatty ester of sucrose. The viscosity of the aqueous solution of a fatty ester of sucrose having a concentration of 9.5% thus prepared was then measured. The results are set forth in Table 1.

COMPARATIVE EXAMPLE 5

The procedure of Example 4 was followed except that the viscosity depressant (monoglyceride of succinic acid) was not added. The viscosity of the aqueous solution of a fatty ester of sucrose thus prepared was then measured. The results are set forth in Table 1.

EXAMPLE 5

The procedure of Example 1 was followed except that Ryoto Sugar Ester L-595 (a fatty ester of sucrose available from Mitsubishi-Kagaku Foods Corporation; HLB: 5, lauric acid content: 95%) was used as the fatty ester of sucrose. The viscosity of the aqueous solution of a fatty ester of sucrose having a concentration of 9.5% thus prepared was then measured. The results are set forth in Table 1.

COMPARATIVE EXAMPLE 6

The procedure of Example 5 was followed except that the viscosity depressant (monoglyceride of succinic acid) was not added. The viscosity of the aqueous solution of a fatty ester of sucrose thus prepared was then measured. The results are set forth in Table 1.

EXAMPLE 6

The procedure of Example 1 was followed except that 9.5 parts of Ryoto Sugar Ester S-1670 (a fatty ester of sucrose available from Mitsubishi-Kagaku Foods Corporation; HLB: 16, stearic acid content: 70%, palmitic acid content: 30%) was used as the fatty ester of sucrose and 0.5 part of the potassium salt of lactylstearic acid (PSL) was used as a viscosity depressant. The viscosity of the aqueous solution of a fatty ester of sucrose having a concentration of 9.5% thus prepared was then measured. The results are set forth in Table 1.

TABLE 1

| Example No. | Fatty ester of sucrose (SE) | | | Viscosity depressant | Added amount (based on wt % of SE) | Viscosity of aqueous solution (cps) |
| | Constituent fatty acid (weight ratio) | HLB | Concentration (%) | | | |
| --- | --- | --- | --- | --- | --- | --- |
| Example 1 | S/P (70/30) | 16 | 9.5 | SMG | 5.3 | 3.6 |
| Comparative Example 1 | S/P (70/30) | 16 | 9.5 | None | — | 320 |
| Comparative Example 2 | S/P (70/30) | 16 | 9.5 | Nonionic | 5.3 | 380 |
| Example 2 | S/P (70/30) | 11 | 9.5 | SMG | 5.3 | 21.3 |
| Comparative Example 3 | S/P (70/30) | 11 | 9.5 | None | — | 960 |
| Example 3 | P[*1] | 5 | 9.5 | SMG | 5.3 | 149 |
| Comparative Example 4 | P[*1] | 5 | 9.5 | None | — | Solidified |
| Example 4 | M[*2] | 5 | 9.5 | SMG | 5.3 | 12 |
| Comparative Example 5 | M[*2] | 5 | 9.5 | None | — | 179 |
| Example 5 | L[*3] | 5 | 9.5 | SMG | 5.3 | 134 |

TABLE 1-continued

| Example No. | Fatty ester of sucrose (SE) Constituent fatty acid (weight ratio) | HLB | Concentration (%) | Viscosity depressant | Added amount (based on wt % of SE) | Viscosity of aqueous solution (cps) |
|---|---|---|---|---|---|---|
| Comparative Example 6 | L*3 | 5 | 9.5 | None | — | 1152 |
| Example 6 | S/P (70/30) | 16 | 9.5 | PSL | 5.3 | 5.7 |

Note:
*1Palmitic acid content: not less than 99%
*2Myristic acid content: 90%
*3Lauric acid content: 95%
SMG Monoglyceride of succinic acid as an anionic surface active agent
Nonionic Poly(oxyethylene)lauryl ether as a nonionic surface active agent
PSL Potassium salt of lactostearic acid ester as an anionic surface active agent
S Stearic Acid
P Palmitic Acid
M Myristic Acid
L Lauric Acid

COMPARATIVE EXAMPLE 7

To 9.5 parts of Emasol P-10 (F) (mainly composed of the monoester of palmitic acid, available from Kao Corp.; HLB: 6.7) as a fatty ester of sorbitan was added 0.5 part (5.3% based on the weight of Emasol P-10 (F)) of the monoglyceride of succinic acid. To the mixture were then added 90 parts of water. The mixture was heated to a temperature of from 70° C. to 80° C. and stirred at this temperature for 20 minutes to make a solution. The aqueous solution was then rapidly cooled to a temperature of 15° C. to obtain a 9.5% aqueous solution of Emasol P-10 (F). The viscosity of the aqueous solution of Emasol P-10 (F) having a viscosity depressant incorporated therein was then measured. As a result, it was found that the aqueous solution thus obtained exhibited a higher viscosity than an aqueous solution having the same composition but free of the viscosity depressant. The results are set forth in Table 2.

COMPARATIVE EXAMPLE 8

The procedure of Comparative Example 6 was followed, except that as the fatty ester of sorbitan Emasol S-10 (F) (mainly composed of the monoester of stearic acid, available from Kao Corp; HLB: 4.7) was used as the ester sorbitan fatty acid. As a result, a 9.5% aqueous solution of Emasol S-10 (F) was obtained. The viscosity of the aqueous solution of Emasol S-10 (F) having a viscosity depressant incorporated therein was then measured. As a result, it was found that the aqueous solution thus obtained exhibited a higher viscosity than an aqueous solution having the same composition but free of the viscosity depressant. The results are set forth in Table 2.

TABLE 2

| Example No. | Fatty ester of sorbitan (SE) Constituent fatty acid (weight ratio) | HLB | Concentration (%) | Viscosity depressant | Added amount (based on wt % of SE) | Viscosity of aqueous solution (cps) |
|---|---|---|---|---|---|---|
| Comparative Example 7 | (P)*4 | 6.7 | 9.5 | SMG None | 5.3 — | 7066 6042 |
| Comparative Example 8 | (S)*5 | 4.7 | 9.5 | SMG None | 5.3 — | 7240 6051 |

Note:
*4Emasol P-10 (F)
*5Emasol S-10 (F)
S Stearic Acid
P Palmitic Acid

EXAMPLE 7

To 20 parts of Ryoto Sugar Ester S-1670 (a fatty ester of sucrose available from Mitsubishi-Kagaku Foods Corporation; HLB: 16, stearic acid content: 70%, palmitic acid content: 30%) was added 1 part (5% based on the weight of the fatty ester of sucrose) of the monoglyceride of succinic acid (SMG) as a viscosity depressant. To the mixture were then added 79 parts of water. The mixture was then stirred. The mixture was heated to a temperature of from 70° C. to 80° C. and was stirred at this temperature for 20 minutes to make a solution. The solution was then rapidly cooled to a temperature of 15° C. to obtain an aqueous solution of a fatty ester of sucrose having a concentration of 20%. The viscosity of the aqueous solution of a fatty ester of sucrose comprising a viscosity depressant incorporated therein was then measured. The viscosity was 2,048 cps.

COMPARATIVE EXAMPLE 9

To 20 parts of Ryoto Sugar Ester S-1670 (a fatty ester of sucrose available from Mitsubishi-Kagaku Foods Corporation; HLB: 16, stearic acid content: 70%, palmitic acid content: 30%) were added 80 parts of water. The mixture was then stirred. The mixture was heated to a temperature of from 70° C. to 80° C. and was stirred at this temperature for 20 minutes to make a solution. The aqueous solution was then rapidly cooled to a temperature of 15° C. to obtain an aqueous solution of a fatty ester of sucrose having a concentration of 20%. The viscosity of the aqueous solution of a fatty ester of sucrose thus obtained was then measured. The viscosity was 4,015 cps.

EXAMPLE 8

To 30 parts of Ryoto Sugar Ester S-1670 (a fatty ester of sucrose available from Mitsubishi-Kagaku Foods Corporation; HLB: 16, stearic acid content: 70%, palmitic acid content: 30%) was added 1.5 parts (5% based on the weight of the fatty ester of sucrose) of the monoglyceride of succinic acid (SMG) as a viscosity depressant. To the mixture were then added 68.5 parts of water. The mixture was then stirred. The mixture was heated to a temperature of from 70° C. to 80C. and was stirred at this temperature for 20 minutes to make a solution. The solution was then rapidly cooled to a temperature of 15° C. to obtain an aqueous solution of a fatty ester of sucrose having a concentration of 30%. The viscosity of the aqueous solution of a fatty ester of sucrose comprising the viscosity depressant incorporated therein was then measured. The viscosity was 8,192 cps.

COMPARATIVE EXAMPLE 10

To 30 parts of Ryoto Sugar Ester S-1670 (a fatty ester of sucrose available from Mitsubishi-Kagaku Foods Corporation; HLB: 16, stearic acid content: 70%, palmitic acid content: 30%) were added 70 parts of water. The mixture was then stirred. The mixture was heated to a temperature of from 70° C. to 80° C. and was stirred at this temperature for 20 minutes to make a solution. The aqueous solution was then rapidly cooled to a temperature of 15° C. to obtain an aqueous solution of a fatty ester of sucrose having a concentration of 30%. The viscosity of the aqueous solution of a fatty ester of sucrose thus obtained was then measured. The viscosity was 16,794 cps.

APPLICATION EXAMPLE 1

21.3 parts of the aqueous solution of a fatty ester of sucrose having a viscosity of 3.6 cps at 15° C. obtained in Example 1 were added to a calcium carbonate slurry having a solids content of 13.3% and an average particle diameter of 4.9 μm. The mixture was then stirred to make a suspension. The suspension was then subjected to grinding/dispersion in a ball mill for 2 hours to obtain a dispersion of particulate calcium carbonate having a calcium carbonate content of 10.2%, a sucrose fatty acid ester content of 1.46%, a succinic acid monoglyceride content of 0.07% and an average particle diameter of 0.42 μm. The dispersion thus obtained was still stable after 30 days of storage.

The suspension was stored at a temperature of 25° C. for 7 days, and then incorporated into milk in an amount such that the calcium content reached 250 mg per 100 g of the milk drink to prepare a calcium-enriched milk. The calcium-enriched milk thus prepared was packed into a heat-resistant glass bottle, and then stored at a temperature of 5° C. for 7 days. The milk was then readily removed from the bottle. The bottom of the bottle was then examined for precipitation. As a result, no precipitation was observed.

COMPARATIVE APPLICATION EXAMPLE 1

21.3 parts of the aqueous solution of a fatty ester of sucrose having a viscosity of 320 cps at 15° C. obtained in Comparative Example 1 were added to a calcium carbonate slurry having a solids content of 13.3% and an average particle diameter of 4.9 μm. The mixture was then stirred to make a suspension. The suspension was then subjected to grinding/dispersion in a ball mill for 2 hours to obtain a dispersion of particulate calcium carbonate having a calcium carbonate content of 10.2%, a sucrose fatty acid ester content of 1.53% and an average particle diameter of 0.45 μm. The dispersion thus obtained showed precipitation after 5 days of storage.

The suspension thus prepared was then immediately incorporated into milk in an amount such that the calcium content reached 250 mg per 100 g of the milk drink to prepare a calcium-enriched milk. The calcium-enriched milk thus prepared was packed into a heat-resistant glass bottle, and then stored at a temperature of 5° C. for 7 days. The milk was then readily removed from the bottle. The bottom of the bottle was then examined for precipitation. As a result, some precipitation was observed.

APPLICATION EXAMPLE 2

An aqueous solution comprising 3 parts of Ryoto Sugar Ester S-1670 (a fatty ester of sucrose available from Mitsubishi-Kagaku Foods Corporation; HLB: 16, stearic acid content: 70%, palmitic acid content: 30%), 0.3 part (10% based on the weight of the fatty ester of sucrose) of the monoglyceride of succinic acid and 17.3 parts of water was prepared as an aqueous solution of an emulsifying agent. 20.6 parts of the aqueous solution thus prepared were then added to 4 parts of propylene glycol as a humectant with 0.4 part of water. The mixture was heated to a temperature of 70° C. and was stirred at this temperature to prepare 25 parts of an aqueous phase.

Separately, 5 parts of solid paraffin, 10 parts of beeswax, 15 parts of vaseline and 44.5 parts of liquid paraffin were mixed. The mixture was heated to a temperature of 70° C. and was stirred at this temperature to prepare 74.5 parts of a homogeneous oil phase. To the oil phase were then added 0.5 part of a perfume and 0.5 parts of butyl paraoxybenzoate as an antiseptic.

The oil phase thus obtained was then added dropwise to the foregoing aqueous phase with stirring. The mixture was then stirred for 1 hour. The mixture was then cooled to a temperature of 20° C. to obtain a cold cream. Portions of 20 parts each were transferred into vessels which were then stored in a high temperature chamber having a temperature of 40° C. and a relative humidity of 65% for 6 months. As a result, the cold cream showed no oil phase/aqueous phase separation in any of these vessels.

As described above, a highly concentrated aqueous solution of a fatty ester of sucrose of the present invention comprising an anionic surface active agent as a viscosity depressant has a lower viscosity than an aqueous solution of a fatty ester of sucrose having the same concentration but which is free of such a viscosity depressant. Thus, the present invention provides improved storability in the form of a highly concentrated aqueous solution of a fatty ester of sucrose and improved workability during stirring and mixing. Furthermore, the highly concentrated aqueous solution of a fatty ester of sucrose having a viscosity thus reduced still exerts good emulsifying and dispersing effects.

While the invention has been described in detail and with reference to specific embodiments thereof, it will be apparent to one skilled in the art that various changes and modifications can be made therein without departing from the spirit and scope thereof.

What is claimed is:

1. A process for reducing the viscosity of an aqueous solution of a fatty ester of sucrose, which comprises incorporating an anionic surface active agent into an aqueous solution containing from 8 to 50% by weight of a fatty ester of sucrose having an hydrophilic-lipophilic balance of from 5 to 20 in an amount of from 1 to 50 parts by weight based on 100 parts by weight of said fatty ester of sucrose, wherein said anionic surface active agent is a salt of an organic acid selected from the group consisting of a fatty acid, a lactylate fatty acid, a monoglyceride of citric acid, a monoglyceride of succinic acid, a monoglyceride of diacetyltartaric acid, stearyl ester of fumaric acid, a stearoyltartaric acid, a stearoylcitric acid, dioctylsulfosuccinate or laurylsulfate, wherein said anionic surface active agent reduces the viscosity of said aqueous solution of a fatty ester of sucrose to not more than two thirds of its initial value in the absence of said anionic surface active agent.

2. The process for reducing the viscosity of an aqueous solution of a fatty ester of sucrose according to claim 1, wherein the viscosity of the aqueous solution of a fatty ester of sucrose containing said anionic surface active agent is not more than 10,000 centipoise (cps) as determined at a temperature of 15° C. by an E type rotary viscometer.

3. The process for reducing the viscosity of an aqueous solution of a fatty ester of sucrose according to claim 1, which comprises adding water to a mixture of a fatty ester of sucrose and an anionic surface active agent, and then heating the mixture to a temperature of from 70° C. to 80° C. so that said fatty ester of sucrose is dissolved to prepare an aqueous solution thereof.

4. The process for reducing the viscosity of an aqueous solution of a fatty ester of sucrose according to claim 1, wherein said anionic surface active agent comprises monoglyceride succinate.

5. The process for reducing the viscosity of an aqueous solution of a fatty ester of sucrose according to claim 1, wherein said fatty ester of sucrose comprises a fatty ester formed from a carboxylic acid comprising from 50 to 90% by weight of stearic acid and from 10 to 50% by weight of palmitic acid.

6. The process for reducing the viscosity of an aqueous solution of a fatty ester of sucrose according to claim 1, wherein said anionic surface active agent is a salt of a monoglyceride of succinic acid.

7. A process for dispersing a particulate inorganic compound, cosmetic material or substance which is sparingly soluble in water which comprises:
(a) providing an emulsifying agent consisting essentially of an aqueous solution containing from 8 to 50% by weight of a fatty ester of sucrose having an hydrophilic-lipophilic balance of from 5 to 20 and an anionic surface active agent in an amount of from 1 to 50 parts by weight based on 100 parts by weight of said fatty ester of sucrose; and
(b) dispersing said inorganic compound, cosmetic material or substance which is sparingly soluble in water in a media containing said emulsifying agent , wherein said anionic surface active agent is a salt of an organic acid selected from the group consisting of a fatty acid, a lactylate fatty acid, a monoglyceride of citric acid, a monoglyceride of succinic acid, a monoglyceride of diacetyltartaric acid, stearyl ester of fumaric acid, a stearoyltartaric acid, a stearoylcitric acid, dioctylsulfosuccinate or laurylsulfate, wherein said anionic surface active agent reduces the viscosity of said aqueous solution of a fatty ester of sucrose to not more than two thirds of its initial value in the absence of said anionic surface active agent.

8. The process according to claim 7, wherein the content of said anionic surface active agent in said emulsifying agent is from 1 to 20 parts by weight based on 100 parts by weight of said fatty ester of sucrose.

9. The process according to claim 8, wherein said emulsifying agent comprises an aqueous solution containing from 8 to 45.5% by weight of a fatty ester of sucrose, from 0.1 to 9% by weight of an anionic surface active agent and from 45.5 to 91.9% by weight of water.

10. The process according to claim 7, wherein said media is an aqueous solution.

11. The process according to claim 7, which comprises dispersing said inorganic compound, cosmetic material or substance in said emulsifying agent.

12. The process according to claim 7, wherein said media is an oil-in-water type emulsion.

13. The process according to claim 7, wherein said anionic surface active agent is a salt of a monoglyceride of succinic acid.

* * * * *